United States Patent [19]

Nowogrodzki

[11] 4,138,998
[45] Feb. 13, 1979

[54] INDICATING TEMPERATURE WITHIN LIVING TISSUE

[75] Inventor: Markus Nowogrodzki, Sussex, N.J.

[73] Assignee: RCA Corporation, New York, N.Y.

[21] Appl. No.: 715,220

[22] Filed: Aug. 18, 1976

[51] Int. Cl.² .............................................. A61B 5/00
[52] U.S. Cl. .................... 128/2 H; 128/404; 128/303.17
[58] Field of Search .............. 128/20, 404, 413, 422, 128/303.17, 2 H; 340/228 R, 228 F; 219/10.55 R, 10.55 M, 10.55 E; 236/88

[56] References Cited

U.S. PATENT DOCUMENTS

| | | | |
|---|---|---|---|
| 2,407,690 | 9/1946 | Southworth | 128/422 |
| 3,491,596 | 1/1970 | Dean | 73/362 SC |
| 3,653,385 | 4/1972 | Burton | 128/303.17 |
| 3,662,140 | 5/1972 | Jones et al. | 219/10.55 B |
| 3,893,111 | 7/1975 | Cotter | 128/2 H |
| 3,975,720 | 8/1976 | Chen et al. | 219/10.55 E |

FOREIGN PATENT DOCUMENTS

| | | | |
|---|---|---|---|
| 1284528 | 12/1968 | Fed. Rep. of Germany | 128/1.5 |
| 149914 | 12/1961 | U.S.S.R. | 73/355 R |

OTHER PUBLICATIONS

Barrett, A. H. et al., "Subcutaneous Temperatures: A Method of Non-Invasive Sensing", Science, V. 190, 11/14/75, pp. 669-670, 685.
Larsen, L. et al., "A Microwave De-coupled Brain--Temperature Transducer", IEEE Trans. on Microwave Theory & Techniques, vol. MTT-ZZ, No. 4, pp. 438-444, Apr. 1974.
Zimmer, R. P. et al., "Selective Electromagnetic Heating of Tumors in Animals in Deep Hypothermia", IEEE Transactions on Microwave Theory & Techniques, vol. MTT-19, No. 2, pp. 238-245, Feb. 1974.
"Microwave Heating of Malignant Mouse Tumors and Tissue Equivalent Phantom Systems", Robinson, McCulloch & Edelsack, Jrnl. of Microwave Power, vol. 11, No. 2, pp. 87-98, 6/76.
"Absence of Heart-rate Effects in Rabbits During Low-level Microwave Irradiation", Kaplan, Metlay, Zaret, Birenbaum, Rosenthal, IEEE Transactions on Microwave Theory and Techniques, vol. MTT-19, No. 2, Feb. 1971, pp. 168-173.

Primary Examiner—Robert W. Michell
Assistant Examiner—Francis J. Jaworski
Attorney, Agent, or Firm—H. Christoffersen; Joseph D. Lazar; John P. McMahon

[57] ABSTRACT

A reflector that reflects a microwave signal as a function of temperature is implanted within living tissue of a human. A microwave signal is transmitted to the reflector via an applicator in contact with the skin of the human. A portion of the signal reflected from the reflector is coupled via the applicator to a meter that provides an indication of the temperature of the reflector.

4 Claims, 7 Drawing Figures

INDICATING TEMPERATURE WITHIN LIVING TISSUE

BACKGROUND OF THE INVENTION

1. Field of Invention

This invention relates to temperature measurement and more particularly to providing an indication of a temperature within living tissue.

2. Description of the Prior Art

When a patient has a cancerous tumor, a surgical procedure is often employed to remove the tumor. However, the surgical procedure may cause a spread of cancer throughout the body of the patient. Therefore, a surgical procedure may be undesirable.

Since ancient times, medical practitioners have known that the patient may be successfully treated by raising the temperature of a tumor, a treatment generally referred to as hyperthermia. One form of hyperthermia is the elevation of the temperature of a large portion of the patient's body where the tumor is located. Accordingly, in the late 1960's, medical practitioners treated patients with tumors in their arms and legs by a profusion therethrough of hot blood. Additionally, patients with tumors in their bladders were treated by flushing the bladders with hot fluid. In 1974 Scottish medical practitioners immersed patients in hot wax. Other medical practitioners have elevated the body temperature of patients by infecting them with malaria. The tumor either shrinks or disappears at a temperature of 43° C. However, elevation of the temperature of a large portion of the body to 42.5° C. may cause death (37° C. is usually referred to as a normal body temperature). Therefore, the elevation of the temperature of a large portion of the body has been only moderately successful.

Although the elevation of a large portion of the human body above a temperature of 42.5° C. may cause death, local tissue of the human body including the tumor may safely withstand temperatures above 43° C. Accordingly, another form of hyperthermia is the elevation of the temperature of the local tissue including the tumor, thereby raising the temperature of the tumor. An early practitioner, Hippocrates, (around 600 B.C.) attempted to raise the temperature of the tumor via conduction by applying red hot irons to the skin. Hippocrates found, and modern medical practitioners have learned, that when the tumor is two centimeters beneath the skin, for example, heating the tumor to about 43° C. via conduction may cause either severe burns or death.

American medical practitioners have used microwave radiation to elevate the temperature of the tissue including the tumor. The microwave radiation may be controlled to rapidly elevate the temperature of a known volume of tissue that extends from the surface of the skin to a known depth beneath the skin. While microwave radiation is used, it is desirable to prevent an over heating that may damage the tissue including the tumor. Therefore, it is correspondingly desirable to provide an indication of the temperature of the tissue including the tumor. Heretofore, suitable apparatus for providing an indication of a temperature of a tissue beneath the skin has not been available in the art.

SUMMARY OF THE INVENTION

According to the present invention, a reflector that reflects a microwave signal as a function of temperature is adapted for implantation within living tissue. In one specific embodiment, a microwave signal is transmitted to the reflector through the tissue via an applicator that is in contact with the tissue. A portion of the signal is reflected from the reflector through the tissue, via the applicator, to a meter that provides an indication of temperature of the tissue near the reflector.

DESCRIPTION OF THE PREFERRED EMBODIMENT

Figure 1:
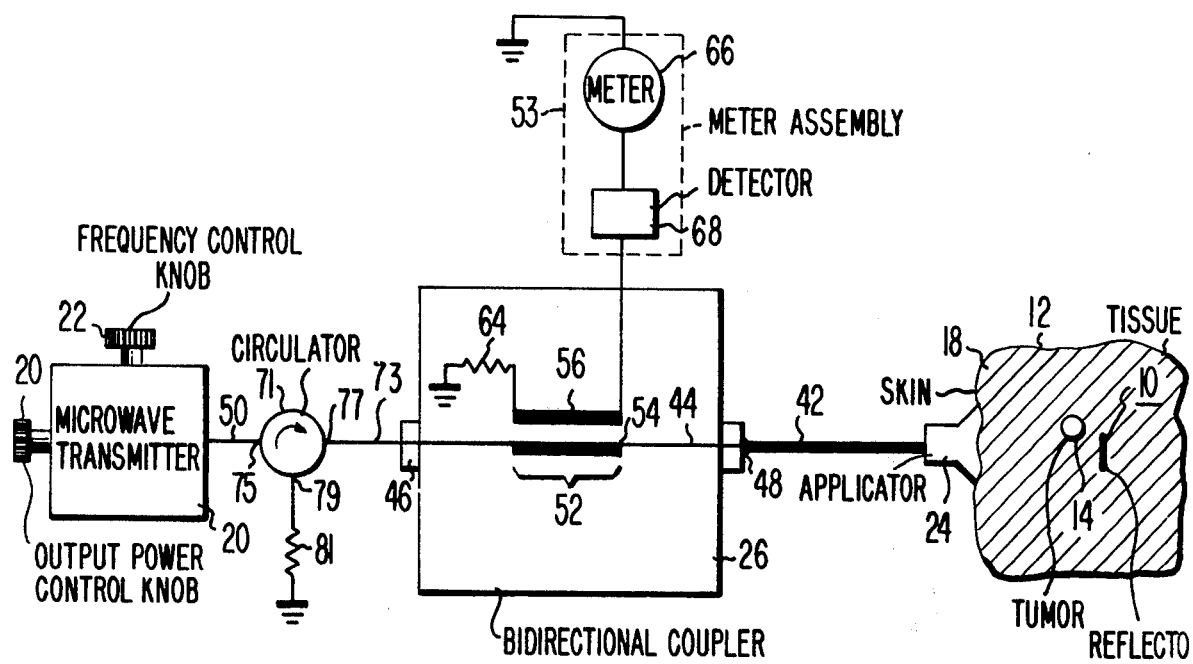
FIG. 1 is a schematic block diagram of a preferred embodiment of the present invention.
Figure 2:
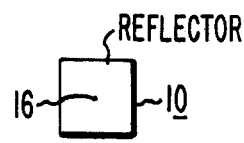
FIG. 2 is a front elevation of a reflector in the embodiment of FIG. 1.

Referring to FIG. 1 and FIG. 2, a surgical procedure is used to implant a reflector 10 within tissue 12 of a patient. The reflector 10 is implanted near a tumor 14 in the tissue 12 whereby the temperature of the reflector 10 is substantially the same as the temperature of the tumor 14. As explained hereinafter, a meter provides an indication of the temperature of the tissue in the vicinity of the reflector 10 as the temperature of the tissue 12 is elevated to (and maintained at) a desired temperature of 43° C. It should be understood that the tissue 12 is normally at a temperature of 37° C.

The reflector 10 is a square wafer of a ferrite material, approximately two and one half millimeters on a side. As known to those skilled in the art, when the temperature of a ferrite material is within a range extending from what is known as a Curie temperature to about 20° C. below the Curie temperature, the level of a microwave signal reflected from the ferrite has a substantial variation as a function of temperature. Accordingly, as will be apparent to those skilled in this art, the changes in the level of the reflected microwave signal are caused by the change in impedance of the ferrite in response to the environmental temperature changes of the tissue in which it is positioned.

Figure 2A:
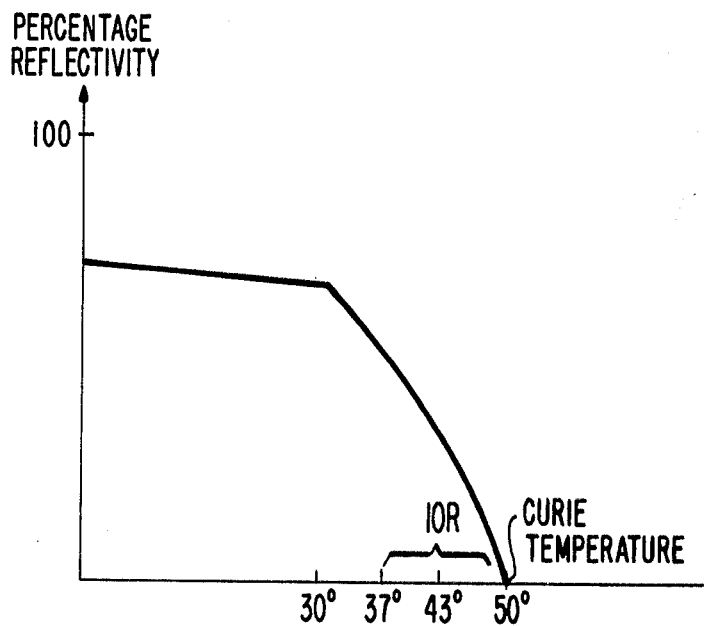
FIG. 2A is a graph of reflectivity as a function of temperature of the reflector of FIG. 1.

Referring to FIG. 2A, in this embodiment, the reflector 10 is comprised of a type of ferrite material, known as lithium-aluminum ferrite, that has a Curie temperature of 50° C. Therefore, the normal temperature (37° C.) and the desired temperature (43° C.) are both within a range 10R that extends from the Curie temperature to 13° C. below the Curie temperature. Accordingly, the normal temperature and the desired temperature are both within a range where there is a substantial variation of the level of the reflected signal as a function of temperature. In one alternative embodiment, the reflector 10 is comprised of a garnet having a compensation temperature of 50° C. In other alternative embodiments, the reflector 10 may be a P-N semiconductor junction or a thermistor.

A flat surface 16 (FIG. 1 and FIG. 2) of the reflector 10 is oriented with respect to a skin surface 18 of the tissue 12 to provide maximum exposure of the reflector 10 to microwave signals applied at the skin surface in the direction of the reflector 10. As explained hereinafter, a microwave signal is transmitted through the skin 18 to heat the tumor 14 to the desired temperature. A portion of the transmitted signal is reflected from the surface 16, whereby a reflected microwave signal passes from the tissue 12 through the skin 18.

The transmitted signal is provided by a microwave transmitter 20 similar to transmitters that are used in microwave ovens and diathermy machines. The transmitted signal penetrates the tissue 12 to a depth beneath the skin 18 that is a function of the frequency of the transmitted signal. Accordingly, the transmitter 20 includes a frequency control knob 22 which is operable to select a transmitted signal frequency in a range of 900 to 3000 megahertz. The frequency range corresponds to a range of depths of penetration of approximately one to three centimeters.

The temperature of the tumor 14 is raised in direct relation to the output power of the transmitter 20. Accordingly, the output power is manually controlled by an output power control knob 23 of the transmitter 20 whereby the temperature of the tumor 14 is manually controlled. The output of the transmitter 20 is connected to an applicator 24 through a circulator 71 and a bidirectional coupler 26, all of which are described hereinafter.

Figure 3:
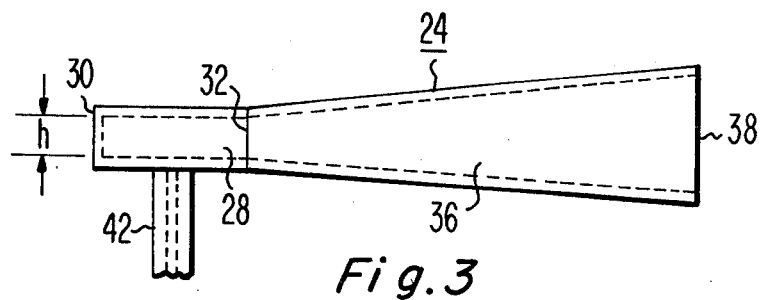
FIG. 3 is a side elevation of an applicator in the embodiment of FIG. 1.
Figure 4:
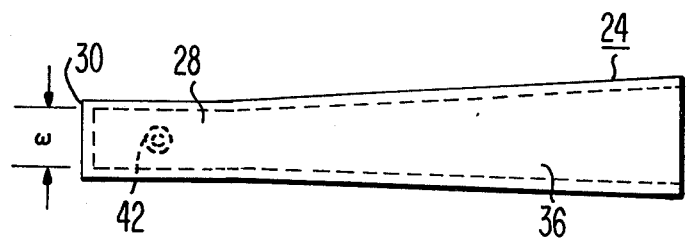
FIG. 4 is a plan view of the applicator of FIG. 3.
Figure 5:
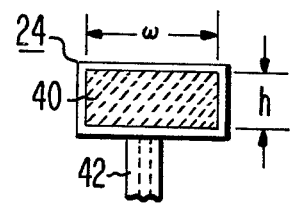
FIG. 5 is an end view of the applicator of FIG. 3.

Referring to FIGS. 3-5, the applicator 24 includes a short section 28 made from WR42 waveguide with an inside width of 1.067 centimeters, an inside height of 0.4018 centimeters and a length of 1.661 centimeters. The section 28 has one end comprised of a conductive plate 30 and another end 32 that is open, whereby electromagnetic waves are reflected from the plate 30 to the end 32. The applicator 24 additionally includes a tapered waveguide section 36 that is 2.99 centimeters long. The section 36 is integrally connected to the section 28 at the end 32 whereby the end 32 is a proximal end of the section 36. A distal end 38 of the section 36 has an inside width of 1.212 centimeters and an inside height of 0.826 centimeters. In this embodiment, the end 38 is maintained in contact with the skin 18.

The applicator 24 is filled with a dielectric material 40 having a dielectric constant that substantially equals the dielectric constant of the tissue 12. Typically, the dielectric constant of the material 40 (and the tissue 12) is in a range of 35 to 85. The section 28 is connected to the bidirectional coupler 26 through a 50 ohm coaxial connector 42 of any suitable type. The applicator 24 substantially matches the impedance of the connector 42 to the impedance of the tissue 12. The applicator 24 can be similar to an applicator that is the subject of a U.S. Pat. application, Ser. No. 671,554, filed on Mar. 29, 1976, and assigned to RCA Corporation, the assignee of the instant application, now abandoned. This application is hereby incorporated herein and made a part hereof. In an alternative embodiment, the applicator 24 can be a rectangular waveguide filled with the dielectric material 40.

The circulator 71 is a microstrip circulator of the type described in U.S. Pat. No. 3,456,213 which is incorporated herein and made a part hereof.

The circulator 71 has ports 75,77 coupled to the transmitter 20 and the bidirectional coupler 26, respectively, via transmission lines 50,73, . Additionally, a port 79 of the circulator 71 is connected through a load resistor 81 to ground. The circulator 71 couples the transmitted signal to the bidirectional coupler 26; a signal from the bidirectional coupler 26 is coupled to the resistor 81.

The bidirectional coupler 26 (FIG. 1) includes a transmission line 44 that extends from an input coupling terminal 46 of the bidirectional coupler 26 to a coupling terminal 48 thereof. The input terminal 46 is connected to a circulator 71 through the transmission line 73 referred to hereinbefore. Accordingly, a signal from the transmitter 20 is transmitted to the reflector 10 via the lines 44,50,73, the circulator 71, the connector 42, the applicator 24 and the tissue 12. Similarly, the reflected signal is received at the terminal 48 from the reflector 10 via the tissue 12, the applicator 24 and the connector 42.

Figure 6:
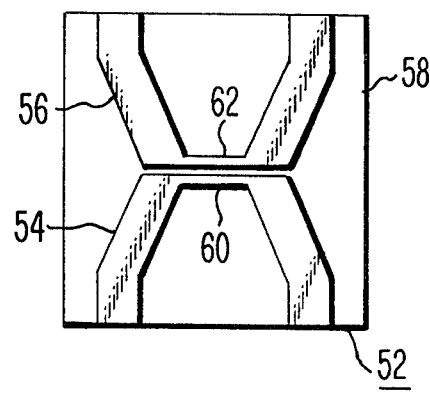
FIG. 6 is a plan view of a coupling section of a bidirectional coupler in the embodiment of FIG. 1.

A coupling section 52 of the bidirectional coupler 26 couples a portion of the reflected signal to a meter assembly 53 as explained hereinafter. Referring to FIG. 6, the coupling section 52 can be comprised of similar copper conductors 54,56, about two mils thick, spaced from a ground conductor by an alumina substrate 58. It should be understood that the conductor 54 is included in the line 44 referred to hereinbefore (FIG. 1). The conductors 54,56 include similar sections 60,62, respectively, that have a length of about one quarter of the wavelength of the transmitted signal. Additionally, the sections 60,62, have a width of approximately 8 mils and a separation therebetween of about 1 mil; all other portions of the conductors 54,56, have a width of about 25 mils.

Referring to FIG. 1, one end of the conductor 56 is connected through a terminating resistor 64 to ground; the other end is connected to the meter assembly 53 to ground. An inherent property of the coupling section 52 is that a portion of the reflected signal is coupled to the meter assembly 53, the remainder of the reflected signal being coupled to the resistor 81 whereby the reflected signal is absorbed by the meter assembly 53 and the resistor 81; substantially none of the reflected signal is coupled to the resistor 64. Correspondingly, a small portion of the transmitted signal is coupled to the resistor 64, most of the transmitted signal being transmitted to the tissue 12 as described hereinbefore; substantially none of the transmitted signal is coupled to the meter assembly 53. Hence, the bidirectional coupler 26 couples the transmitted signal to the tissue 12 and not to the meter assembly 53 whereas the reflected signal is coupled to the meter assembly 53. Various forms of the bidirectional coupler 26 suitable for use in the instant application are available in the art and the coupler itself forms no part of the instant invention.

The meter assembly 53 is comprised of a meter 66 connected in series with a detector 68. The detector 68 rectifies the portion of the reflected signal coupled to the meter assembly 53 whereby a d.c. current passes through the meter 66. The d.c. current is proportional to the level of the reflected signal thereby causing the meter 66 to provide an indication of the level of the reflected signal.

What is claimed is:

1. Apparatus for indicating temperature within living tissue, comprising:

impedance varying reflector means responsive to temperature changes for changing its impedance as a function of temperature;

said reflector means adapted for implantation within said tissue for positioning to reflect impinging microwave signals;

a microwave signal transmitter providing said microwave signal to said reflector at a predetermined frequency;

a meter for indicating the level of a reflected microwave signal reflected from said reflector in response to said microwave signal from said transmitter;

applicator means, adapted for contact with said tissue, for providing a substantially matched impedance at a given temperature for coupling microwave signals to and from said tissue; and means for coupling said transmitted microwave signal from said transmitter to said applicator means for application to said tissue and said reflector and for coupling to said meter a microwave signal reflected to said applicator means from said reflector;

whereby said reflector in response to changes in temperature of said tissue from said given temperature will cause the level of said reflected signal to change as a function of said temperature changes in said tissue.

2. Apparatus according to claim 1 wherein said reflector means includes a ferrite material that has a Curie temperature in a range of 43° C. to 55° C.

3. Apparatus according to claim 12 wherein said ferrite material is comprised of a lithium-aluminum ferrite.

4. In the method of providing an indication of temperature within living tissue, the steps of:
transmitting a microwave signal at a predetermined frequency into said tissue;
reflecting a microwave signal from an impedance varying reflector positioned within said tissue, said reflected signal from said reflector having a signal level that is a function of said temperature; and
indicating said reflected signal level as a representation of temperature within said tissue.

* * * * *

UNITED STATES PATENT AND TRADEMARK OFFICE
CERTIFICATE OF CORRECTION

PATENT NO. : 4,138,998

DATED : February 13, 1979

INVENTOR(S) : Markus Nowogrodzki

It is certified that error appears in the above-identified patent and that said Letters Patent is hereby corrected as shown below:

Column 6, line 4 "12" should be --2--.

Signed and Sealed this

Twentieth Day of November 1979

[SEAL]

Attest:

RUTH C. MASON
Attesting Officer

LUTRELLE F. PARKER
Acting Commissioner of Patents and Trademarks